United States Patent [19]

McKay et al.

[11] Patent Number: 4,593,685

[45] Date of Patent: Jun. 10, 1986

[54] BONE CEMENT APPLICATOR

[75] Inventors: William F. McKay, Budd Lake, N.J.; Peter S. Walker, Weston, Mass.

[73] Assignee: Pfizer Hospital Products Group Inc., New York, N.Y.

[21] Appl. No.: 542,621

[22] Filed: Oct. 17, 1983

[51] Int. Cl.[4] ............................................. A61F 5/04
[52] U.S. Cl. ................................ 128/92 E; 128/92 R
[58] Field of Search ............... 128/92 E, 92 R, 92 BC

[56] References Cited

U.S. PATENT DOCUMENTS

| D. 238,107 | 12/1975 | Heros | D8/30 |
|---|---|---|---|
| 956,929 | 5/1910 | Bradbury | 401/176 |
| 1,296,107 | 3/1919 | Oakley | 401/176 |
| 2,249,401 | 7/1941 | Sieg | 401/176 |
| 2,388,321 | 11/1945 | Gereke | 401/150 |
| 2,578,765 | 12/1951 | Wallace | 401/176 |
| 2,636,214 | 4/1953 | Slusher | 401/176 |
| 3,223,083 | 12/1965 | Cobey | 128/92 R |
| 3,711,448 | 1/1973 | Goodman et al. | 128/92 R |
| 4,093,576 | 6/1978 | de Wijn | 128/92 R |
| 4,223,999 | 9/1980 | Wells | 222/386 |
| 4,277,184 | 7/1981 | Solomon | 128/92 R |
| 4,323,177 | 4/1982 | Nielsen | 222/386 |
| 4,338,925 | 7/1982 | Miller | 128/92 E |
| 4,341,691 | 7/1982 | Anuta | 128/92 R |
| 4,399,814 | 8/1983 | Pratt, Jr. et al. | 128/92 R |
| 4,462,394 | 7/1984 | Jacobs | 128/92 BC |
| 4,466,435 | 8/1984 | Murray | 128/92 E |

OTHER PUBLICATIONS

Bryan et al., "Revision Total Knee Arthroplasty", Clinical Orthopedics (1982) pp. 116-122.

Primary Examiner—Robert Peshock
Assistant Examiner—C. W. Shedd
Attorney, Agent, or Firm—Charles J. Knuth; Peter C. Richardson; Mark Dryer

[57] ABSTRACT

A bone cement applicator for applying a predetermined amount of cement to uniformly penetrate a bone comprising a plunger terminating in an integral flat substantially rigid applicator plate, preferably metallic, and being slidably mounted in a tubular sleeve integral with an open-ended reservoir around the applicator plate, the periphery of said reservoir having a configuration conforming to the bone surface area to which the cement is applied and a method of applying bone cement using said applicator. The applicator is particularly adapted for the application of bone cement in total knee replacement.

9 Claims, 11 Drawing Figures

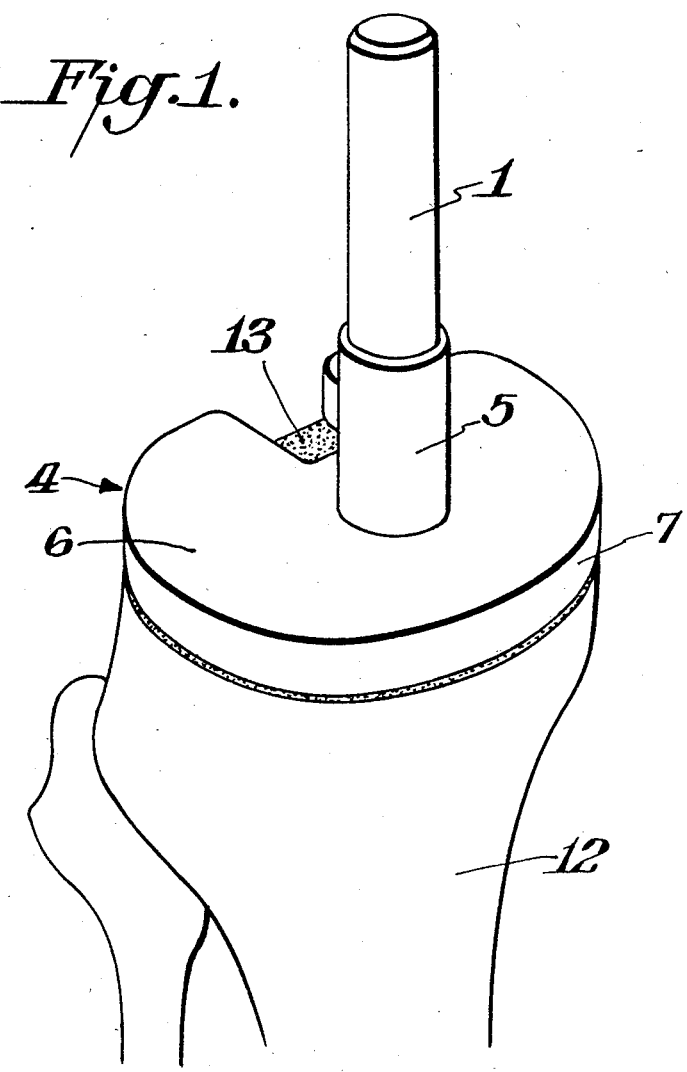
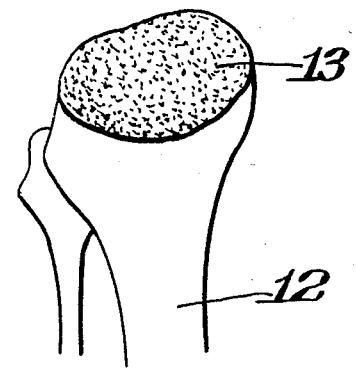
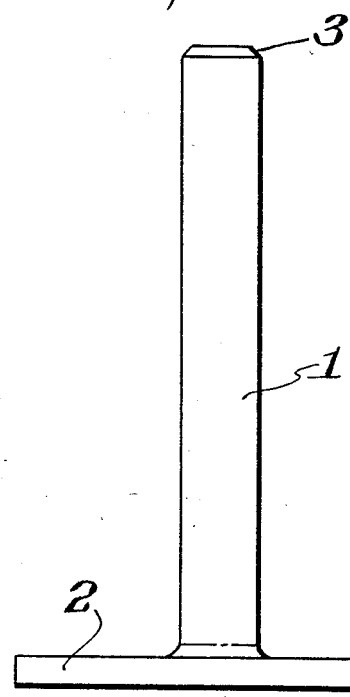
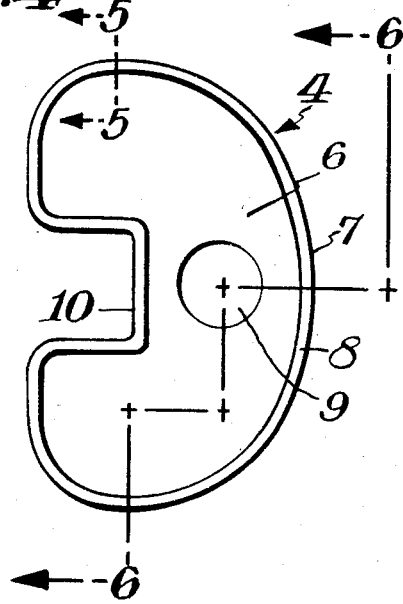
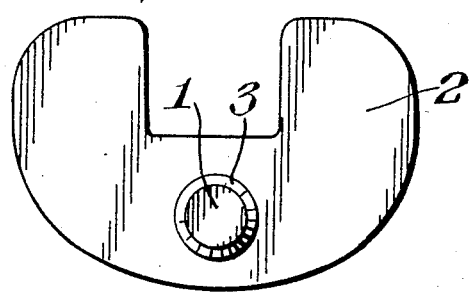

BONE CEMENT APPLICATOR

BACKGROUND OF THE INVENTION

This invention relates to a bone cement applicator for delivering a predetermined amount of cement into a bone to achieve substantially uniform penetration of cement over a predetermined surface-area of the bone, particularly the top of a resected tibia. The invention is also concerned with a method of applying bone cement using such applicator.

The use of prosthetic components involving the cementing of such components to bone, particularly total knee replacement, is taking place with increasing frequency. Accordingly, there is increasing interest in the improvement of cementing techniques to avoid complications arising from loosening of the prosthetic component.

When a prosthetic component is attached to cancellous bone with bone cement, particularly acrylic cement, a bond is formed by the penetration of the cement into the bone. The depth of penetration is dependent upon the pressure under which the cement is applied, the time of pressure application, the viscosity of the cement and the porosity of the bone; and the said depth is a predominant factor in determining the tensile or shear strength of the cement-bone interface.

A problem with total knee replacement is that prosthetic loosening frequently occurs. Loosening of the tibial component has been a serious problem with many of the early prosthetic knees. Such loosening leads to instability and pain. In cases where the loosening was such as to require revision invariably radiolucency was observed at the cement-bone interface. This radiolucency normally signifies a layer of fibrous tissue beneath which is often a thin layer of dense bone. Loose prosthetic components together with cement usually may be lifted from the surface of fibrous tissue, indicating that there is zero tensile bond strength at the interface. Presumably, an initial cement-bone interface of low tensile strength which allowed micromovements to occur between the cement and bone would readily reach this condition, whereas a high initial tensile strength tends to inhibit interface breakdown.

Various methods have been developed to improve the cementing technique and consequently increase the strength of the bone-cement interface in total knee replacement and thus avoid tibial component loosening. However, although relatively good cement penetration has been achieved by past methods in the central areas of the tibia, in contrast, the periphery often shows poor penetration secondary to leakage of cement around the component on insertion. In the past it has proved difficult to achieve adequate cement penetration in sclerotic bone resulting from valgus or varus deformity. These peripheral and sclerotic areas are the earliest and most frequent sites of radiolucencies at the bone-cement interface.

Accordingly, it is an object of the present invention to provide means whereby uniform cement penetration over the entire bone surface is achieved.

SUMMARY OF THE INVENTION

In accordance with the present invention there is provided a bone cement applicator for applying a predetermined amount of cement into a bone to achieve substantially uniform penetration over a predetermined surface area of the bone, which comprises a cylindrical plunger rod perpendicular to and terminating in an integral flat substantially rigid applicator plate, said rod being slidably mounted in a tubular sleeve integral with an open-ended reservoir around the applicator plate, the periphery of said reservoir having a configuration conforming to said bone surface area and the capacity of the reservoir when the plunger is fully retracted conforming to the said predetermined amount of cement.

The applicator of the present invention is designed primarily for use in total knee replacement and, accordingly, in the preferred embodiment the configuration of the open end of the reservoir is adapted to fit the top of a resected tibia. It follows that the applicator plate, which is preferably a metallic dam forming the terminal end of a close-fitting sliding plunger, is preferably made to conform to the average shape of the upper tibia. In the most preferred embodiment this shape is the same as that of a current knee prosthesis design having a recess for the posterior cruciate ligament.

Also in the preferred embodiment it is desirable that the bone-engaging circumferential edge of the reservoir is chamfered so as to form a circumferential edge seal means, to minimize interference with soft tissue surrounding the bone area and to obtain a narrow edge for sealing, thereby achieving a better seating or seal on the resected tibia surface.

The invention also provides a method of applying bone cement to achieve substantially uniform cement penetration with sufficient depth to provide a strong bone-cement interface over a predetermined surface-area of a bone, preferably the top of a resected tibia, by applying bone cement through an applicator as described above, which comprises retracting the applicator plate, charging the reservoir with the predetermined amount of cement to achieve the desired penetration, placing the open end of the reservoir in intimate contact with the bone surface and depressing the plunger until the substantially full charge of cement is injected into the selected part of the bone.

In carrying out the method, preferably said plunger is depressed by striking the proximal end thereof, whereupon said applicator is removed by sliding it from said interface at the completion of cement injection.

BRIEF DESCRIPTION OF THE DRAWINGS

A preferred embodiment of the invention is illustrated in the accompanying drawings, in which:

FIG. 1 is a perspective view of the applicator of the invention positioned on top of a resected tibia;

FIG. 2 is a perspective view of the top end of a tibia illustrating the prepared flat surface;

FIG. 3 is a side elevation of the integral plunger rod and applicator plate of an applicator according to the invention;

FIG. 3A is a top plan of the applicator plate of FIG. 3;

FIG. 4 is a bottom plan of the reservoir of an applicator according to the invention;

DETAILED DESCRIPTION OF THE INVENTION

Figure 4A:
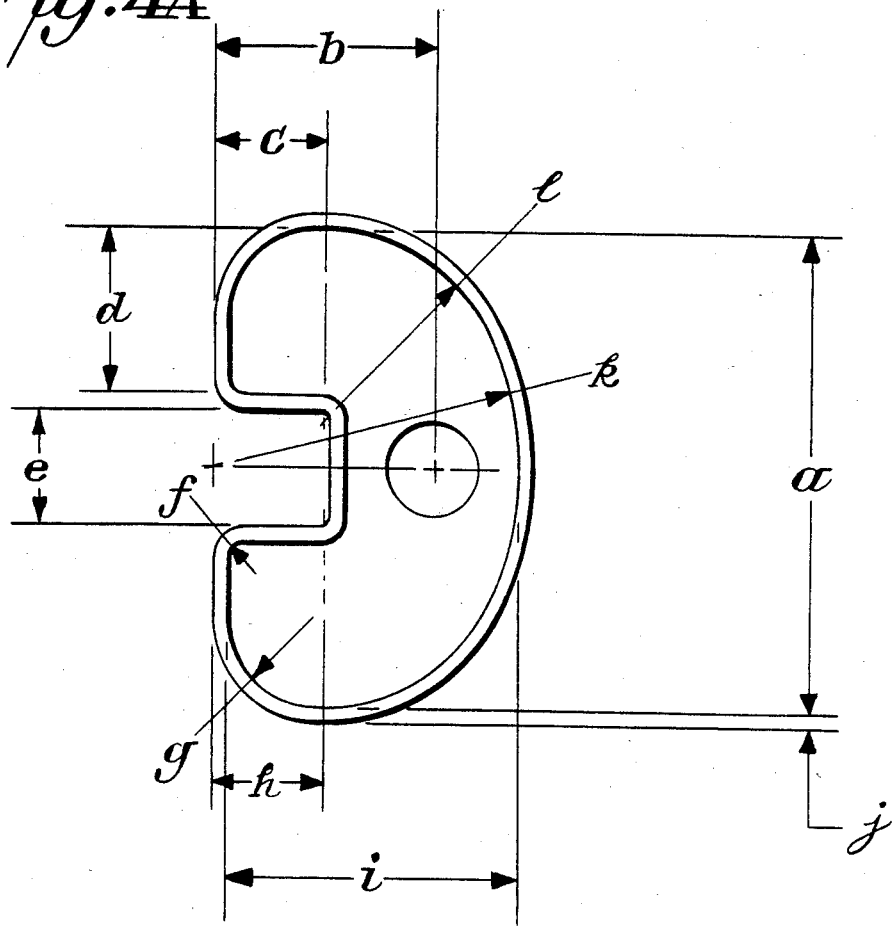
FIG. 4A is the same plan as FIG. 4 but additionally indicating the dimensions of a typical medium sized applicator.

The invention will now be more particularly described with reference to the preferred embodiment illustrated in the drawings.

The applicator illustrated in FIG. 1 and FIG. 3 of the drawings comprises a cylindrical plunger rod 1 perpendicular to and terminating in an integral flat substantially rigid applicator plate 2. The integral combination of plunger rod and applicator plate is normally made of metal, preferably stainless steel.

In carrying out the application of bone cement using an applicator according to the invention the applicator is positioned on the top of a resected tibia 12 whose top surface 13 is substantially flat and has been prepared to receive cement so that the prosthetic component may be bonded thereto. The cement is applied by striking the proximal end of the plunger rod, i.e. the end closest to the user and furthest from the applicator plate. The striking is carried out with a surgical mallet or hammer.

To enable the plunger to withstand the repeated hammering it necessarily must be of a robust structure. Also, since the said hammering tends to flatten or distort the proximal end of the plunger rod, to enable the plunger to be used repeatedly, the said proximal end preferably has a chamfer 3 as illustrated in FIG. 3. The chamfering helps to avoid excess deformation of the proximal end so that the plunger may be slidably inserted in the inside of the tubular sleeve 9 (see FIG. 4) of the outer housing 4 and thus used repeatedly.

In contrast thereto the outer housing 4 is expendable and normally would only be used once.

The outer housing 4 comprises a tubular sleeve 5 within which the plunger rod 1 is slidably mounted. To assemble the applicator, the proximal end of the plunger rod is slidably inserted into the inside 9 of the tubular sleeve from the bottom up.

The lower part of the housing forms a reservoir 6 having an outer wall 7 whose periphery conforms with the surface area of the top of the resected tibia. The bone-engaging edge 8 of the wall 7 preferably is chamfered so as to form a circumferential edge seal means. As indicated hereinbefore this tapering provides a narrow edge for sealing and minimizes interference with soft tissue surrounding the bone area. The said wall 7 also fits around the applicator plate 2 which likewise has a configuration (in plan) which conforms with the surface area of the top of the resected tibia. This configuration has a recess 10 to accomodate the posterior cruciate ligament.

The outer housing 4 preferably is made of a polymeric material, for example polypropylene, and generally is formed by moulding or casting. The use of polypropylene means that the housing is substantially rigid enough to allow the plunger/applicator plate to be depressed by striking the proximal end thereof until the plate bottoms out without any bulging or distortion of the reservoir while the material is still sufficiently resilient to allow the chamfered edge to form a close seal on the surface of the tibia. Also the use of a polypropylene moulding means that the housing is comparitively inexpensive and thus is disposable, thereby avoiding the need of cleaning (from excess cement) and sterilizing for reuse.

Figure 6:
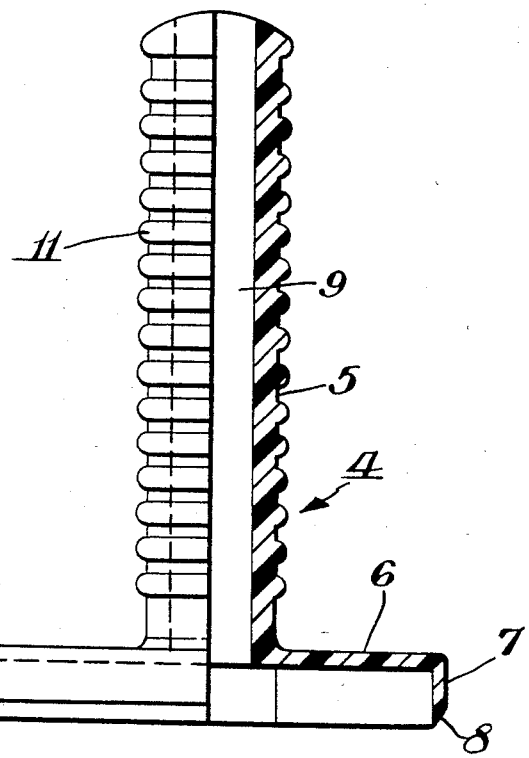
FIG. 6 is a partial cross-section and side elevation taken along lines 6—6 of FIG. 4.

Since a certain amount of pressure is required to hold the housing in place on the tibia while the plunger is being depressed to dispense the cement into the bone, it is preferred that the outer wall of the tubular sleeve 5 be shaped to form a grippable handle, for example as a moulding comprising ridges 11 and grooves as illustrated in FIG. 6 of the drawings.

Figure 5:
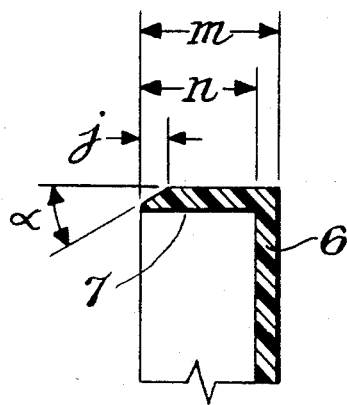
FIG. 5 is a section through 5—5 on FIG. 4.

The dimensions of an applicator according to the invention for applying cement to a resected tibia generally will be dictated by the size of the patient's bones and the present invention is not limited to any particular dimensions. However, it has been found that three standard sizes, small, medium and large, are suitable for most practical cases. The dimensions for a typical medium applicator, with reference to the elements of the housing illustrated in FIG. 4A and FIG. 5 are given in the following Table 1.

TABLE 1

| Dimension (See FIG. 4A & FIG. 5) | Description | Inches | mm |
|---|---|---|---|
| a | reservoir/plate long axis | 2.67 | 67.84 |
| b | partial width | 1.324 | 33.63 |
| c | depth of recess (left) | 0.681 | 17.30 |
| d | distance, edge to recess | 0.901 | 22.89 |
| e | width of recess | 0.749 | 19.02 |
| f | radius of curvature | 0.120 | 3.04 |
| g | radius of curvature | 0.50 | 12.70 |
| h | depth of recess (right) | 0.762 | 19.35 |
| i | internal shorter axis | 1.771 | 44.98 |
| j | wall thickness | 0.06 | 1.5 |
| k | radius of curvature | 1.851 | 47.02 |
| l | radius of curvature | 1.121 | 28.47 |
| m | outer depth | 0.410 | 10.41 |
| n | inner depth | 0.345 | 8.75 |
|  | angle of taper | 30° | |
| FIG. 3 | diameter of plunger rod | 0.56 | 14.22 |
| FIG. 3 | length of plunger rod | 3.91 | 99.31 |
| FIG. 3 | thickness of applicator plate | 0.187 | 4.75 |
| FIG. 6 | length of handle | 3.69 | 93.73 |
| FIG. 6 | outer diameter of ridges 11 | 0.98 | 24.9 |
| FIG. 6 | thickness of ridges 11 | 0.12 | 3.0 |
| FIG. 6 | inner diameter of grooves | 0.86 | 21.8 |

The dimensions for analogous elements of a small or large applicator, except for the thickness of the walls of the housing which is substantially the same, would be decreased or increased, respectively by up to 0.25 inch (or 6.35 mm).

Figure 7:
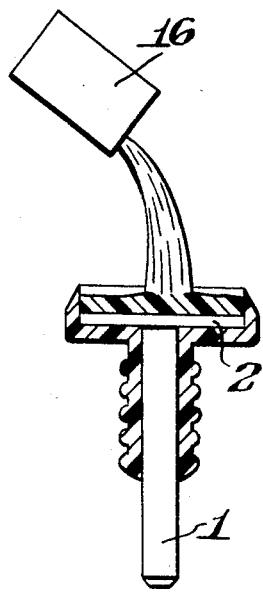
FIGS. 7, 8 and 9 illustrate in schematic form the operation of the applicator in accordance with the method of the invention showing the charging of the reservoir with cement and the position of the applicator plate before and after, respectively, the application of cement into the tibia.
Figure 8:
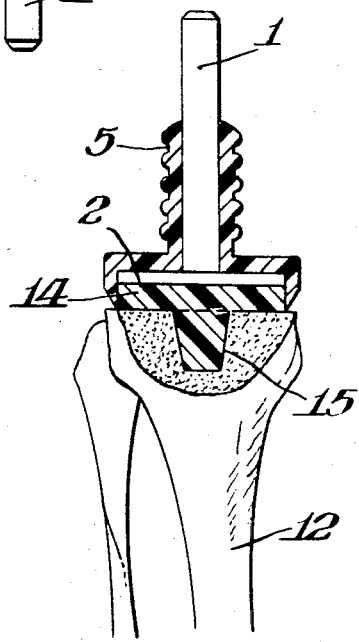
Figure 9:
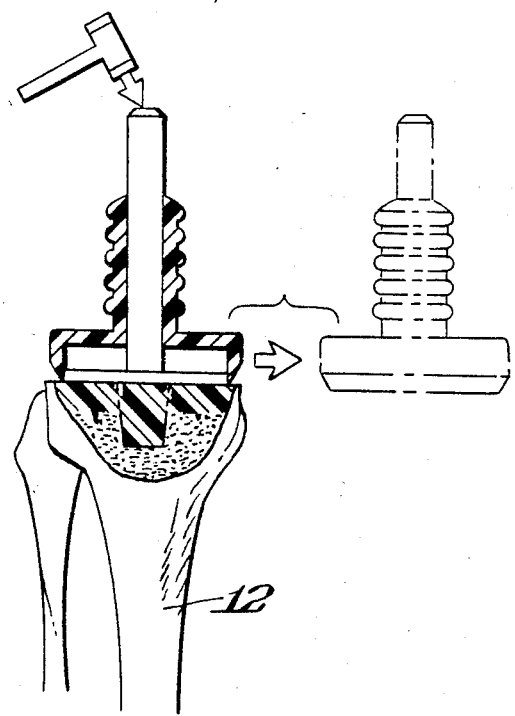

The performance of the method of the invention for applying bone cement to a resected tibia is illustrated schematically in FIG. 7 (charging with cement), FIG. 8 (before depressing the plunger and FIG. 9 (after depressing the plunger).

The plunger comprising rod 1 and applicator plate 2 is first fully retracted and the reservoir is charged with a predetermined amount of bone cement 14 from a container 16, as shown in FIG. 7. As shown in FIG. 8, applicator charged with cement is then positioned on the prepared surface of the tibia to which the cement is to be applied. In preparing the tibia a rectangular slot is cut in the middle of the upper surface for the central peg of the tibial component and a bony plug is pressed into this slot. This central rectangular slot is filled with cement 15 before the applicator is placed on the surface.

After positioning the applicator on the tibia surface the plunger is struck several times by a surgical hammer as illustrated in FIG. 9, until the plunger is felt to bottom out. At this point the applicator was slid off the tibial surface anteriorly. The penetration of cement into the tibia 12 is indicated by the small arrows (not to scale) in FIG. 9.

The advantageous results obtainable by use of the applicator of the invention are indicated by the experiment described in the following Example.

EXAMPLE

Eight human tibias cut about 150 millimeters below the joint line were obtained from non-embalmed cadaver donors. The bones were cleaned of all soft tissue and frozen in saline soaked-towels enclosed in plastic bags. Prior to preparation, the specimens were thawed. The tibias were mounted vertically and the upper surface of each tibia was resected with an oscillating saw at the usual level for implantation of a tibial component, perpendicular to the long axis in frontal and sagital planes. The resection line was about 7 millimeters below the anterior edge and 2 millimeters below the posterior edge. A rectangular slot was cut in the middle of the upper surface for the central peg of the tibial component. A bony plug was pressed into this slot to a depth of 60 millimeters. The bone surface was thoroughly cleaned with a polyethylene brush, irrigated with water and dried with gauze sponges.

Acrylic cement (Simplex P) was mixed at a room temperature of 23° C. and introduced into the retracted applicator after 2-3 minutes of mixing, immediately on initiation of the doughy stage. The central rectangular slot was filled with cement before the applicator was applied. The applicator was then placed on the tibial surface and the plunger was struck several times until the plunger was felt to bottom out. At this point the applicator was slid off the tibial surface anteriorly and an additional layer of cement was placed on the tibial surface for better visualization on sectioning.

When the cement had hardened, five of the tibias were sectioned in six uniform sagital planes while the other three tibias were sectioned in six uniform frontal planes. The upper level of the bony surface was marked with a black line. Each section was then photographed and the depth of cement penetration was measured.

In order to determine the porosity of the tibial surface, the removed tibial tops were smoothed, cleaned and photographed under oblique lighting with high contrast film, which showed bone as white and pore spaces as black.

Generally, the penetration was quite uniform at about 4 millimeters in depth along all of the sections. The results are given in the following Tables 2 and 3.

TABLE 2

The depths of cement penetration in the sagital sections of five tibias (millimeters).

| Section # Medial to Lateral | Anterior | Middle | Posterior | Average (Range) |
|---|---|---|---|---|
| 1 | 4.3 | 3.4 | 3.6 | 3.5 |
|  | (3.0–4.0) | (3.0–4.0) | (3.0–4.0) | (3.0–4.0) |
| 2 | 4.1 | 3.8 | 4.4 | 4.1 |
|  | (3.0–5.0) | (3.0–5.0) | (4.0–5.0) | (3.0–5.0) |
| 3 | 3.7 | 4.4 | 4.2 | 4.1 |
|  | (3.0–5.5) | (3.0–5.5) | (3.0–5.5) | (3.0–5.5) |
| 4 | 3.8 | 2.7 | 4.2 | 3.6 |
|  | (3.0–5.5) | (2.5–3.0) | (3.0–5.0) | (3.0–5.5) |
| 5 | 3.8 | 3.8 | 4.1 | 3.9 |
|  | (3.0–4.0) | (3.0–5.0) | (3.0–5.0) | (3.0–5.0) |
| 6 | 4.1 | 4.4 | 3.3 | 3.9 |
|  | (3.0–5.0) | (3.0–5.0) | (2.5–4.0) | (2.5–5.0) |
| Average | 3.8 | 3.8 | 4.0 |  |

TABLE 2-continued

The depths of cement penetration in the sagital sections of five tibias (millimeters).

| Section # Medial to Lateral | Anterior | Middle | Posterior | Average (Range) |
|---|---|---|---|---|
| Range | (3.0–5.5) | (2.5–5.5) | (2.5–5.5) |  |

TABLE 3

The depths of cement penetration in the frontal sections of three tibias (millimeters).

| Section # Anterior to Posterior | Medial | Middle | Lateral | Average (Range) |
|---|---|---|---|---|
| 1 | 4.2 | 3.5 | 3.8 | 3.8 |
|  | (3.5–5.0) | (3.0–4.5) | (3.5–4.0) | (3.0–5.0) |
| 2 | 3.7 | 3.3 | 3.8 | 3.6 |
|  | (3.0–4.0) | (3.0–4.0) | (3.5–4.0) | (3.0–4.0) |
| 3 | 3.7 | 3.8 | 3.3 | 3.6 |
|  | (3.5–4.0) | (3.5–4.0) | (2.5–4.0) | (2.5–4.0) |
| 4 | 3.3 | 3.3 | 4.0 | 3.6 |
|  | (2.5–4.0) | (3.0–4.0) | (3.0–5.5) | (2.5–5.5) |
| 5 | 3.7 | 3.5 | 3.3 | 3.5 |
|  | (3.0–4.0) | (3.0–4.0) | (2.5–4.5) | (2.5–4.5) |
| 6 | 3.5 | 3.3 | 3.3 | 3.4 |
|  | (2.5–5.0) | (3.0–4.0) | (3.0–3.5) | (2.5–5.0) |
| Average | 3.7 | 3.5 | 3.6 |  |
| Range | (2.5–5.0) | (3.0–4.0) | (2.5–5.0) |  |

As indicated in the above Tables, virtually all of the depths measured were in the range of 3-5 millimeters. The variations were believed to be primarily due to local variations in bone porosity. It was notable that the penetration was uniform up to the very edge of the rim of the applicator. However, in some cases, there was minor leakage at peripheral regions due to irregularity. The fact that this did not seen to affect penetration was probably due to the high hydrostatic cement pressures generated on impacting the plunger. The porosity of the bones spanned a range from high to low porosity, typical of the situation in surgical conditions.

Access of the cement applicator was not a problem. The applicator was introduced after final preparation of the tibial and femoral bone surfaces. This allowed adequate access and visualization, even of the posterior tibia. This applied whether or not the posterior cruciate was resected. The hole for the central peg could be prefilled, in which case there would be a lot of penetration around the peg when the component was introduced, or not filled, in which case there would be some reduced penetration on the upper surface around the hole. A compromise is probably the best solution. The time of the operation is not affected by use of the applicator, since the same batch of cement is used.

The above results show that the cement applicator of the present invention achieved adequate and uniform cement penetration consistently on the upper tibial surface. The penetration was between 2.5 and 5.5 millimeters in all areas, which is within the range of penetration found to be desirable by previous studies. Unlike most other methods, this technique is simple and achieves good penetration in peripheral areas which have been shown to be the earliest and the most frequent sites of radiolucency between the bone and cement interface.

We claim:

1. A bone cement applicator adapted for the application of a predetermined amount of cement solely to a predetermined surface area of a bone in an arthroplasty procedure to achieve substantially uniform penetration over said predetermined surface area of the bone, which comprises a cylindrical plunger rod having an exposed proximal end adapted to be struck for dispensing said cement, said rod being perpendicular to and terminating in an integral flat substantially rigid applicator plate, said rod being slidably mounted in a tubular sleeve integral with an open-ended reservoir around the applicator plate, the periphery of said reservoir having a configuration conforming to said bone surface area and the capacity of the reservoir when the plunger is fully retracted conforming to the predetermined amount of cement.

2. An applicator according to claim 1, in which the configuration of the open end of the reservoir is adapted to fit the top of a resected tibia.

3. An applicator according to claim 1, in which the integral combination of plunger rod and applicator plate is made of metal.

4. An applicator according to claim 3, in which the metal is stainless steel.

5. An applicator according to claim 1, in which the tubular sleeve and reservoir together form an integral outer housing made of a polymeric material.

6. An applicator according to claim 5, in which the polymeric material is polypropylene.

7. An applicator according to claim 5, in which the outside of the tubular sleeve is shaped to form a grippable handle.

8. A method of applying bone cement in an arthroplasty procedure to achieve substantially uniform cement penetration with sufficient depth to provide a strong bone-cement interface over a predetermined surface-area of a bone by applying bone cement through an applicator comprising a cylindrical plunger rod perpendicular to and terminating in an integral flat substantially rigid applicator plate, said rod being slidably mounted in a tubular sleeve integral with an open-ended reservoir around the applicator plate, the periphery of said reservoir having a configuration conforming to said bone surface area and the capacity of the reservoir when the plunger is fully retracted conforming to a predetermined amount of cement to achieve the desired penetration, which method comprises retracting said applicator plate, charging said reservoir with said predetermined amount of cement, placing the open end of said reservoir in intimate contact with the bone surface and depressing said plunger by striking the proximal end thereof until the substantially full charge of cement is injected into the selected part of the bone, whereupon said applicator is removed by sliding it from said interface at the completion of cement injection.

9. A method according to claim 8, in which the bone into which the cement is applied is the top of a resected tibia.

* * * * *